United States Patent
Sakagawa (10) Patent No.: US 11,083,153 B2
(45) Date of Patent: Aug. 10, 2021

(54) SWEET CORN AND METHOD FOR PRODUCING SAME

(71) Applicant: SAKATA SEED CORPORATION, Yokohama (JP)

(72) Inventor: Kohei Sakagawa, Yokohama (JP)

(73) Assignee: SAKATA SEED CORPORATION, Yokohama (JP)

(*) Notice: Subject to any disclaimer, the term of this patent is extended or adjusted under 35 U.S.C. 154(b) by 0 days.

(21) Appl. No.: 16/079,935

(22) PCT Filed: Sep. 21, 2017

(86) PCT No.: PCT/JP2017/034823
§ 371 (c)(1),
(2) Date: Aug. 24, 2018

(87) PCT Pub. No.: WO2018/056471
PCT Pub. Date: Mar. 29, 2018

(65) Prior Publication Data
US 2020/0178489 A1   Jun. 11, 2020

(30) Foreign Application Priority Data
Sep. 26, 2016 (JP) .............................. JP2016-186906

(51) Int. Cl.
*A01H 6/46* (2018.01)
*A01H 5/10* (2018.01)
*A01H 1/00* (2006.01)

(52) U.S. Cl.
CPC .......... *A01H 6/4684* (2018.05); *A01H 1/107* (2021.01); *A01H 1/108* (2021.01); *A01H 5/10* (2013.01)

(58) Field of Classification Search
None
See application file for complete search history.

(56) References Cited

U.S. PATENT DOCUMENTS

| 7,371,930 B1 * | 5/2008 | Knerr .................. A01H 5/12 435/410 |
| 9,635,825 B1 * | 5/2017 | Ahmed .................. A01H 5/10 |
| 2013/0019338 A1 | 1/2013 | Plehn |

FOREIGN PATENT DOCUMENTS

| CN | 105075856 | 11/2015 |
| JP | 2012-514471 A | 6/2012 |
| JP | 2014-520557 | 8/2014 |
| WO | 2011019331 | 2/2011 |

OTHER PUBLICATIONS

Pataky et al. Sweet Corn Disease Nursery: 2001 Annual Report. Crop Sciences. 2001. Table 4 pp. 1-3.*
Duan et al. Dietary supplementation with L-glutamate and L-aspartate alleviates oxidative stress in weaned piglets challenged with hydrogen peroxide. Amino Acids. 2016. 48: 53-64.*

(Continued)

*Primary Examiner* — Ashley K Buran
(74) *Attorney, Agent, or Firm* — Lucas & Mercanti, LLP (57) ABSTRACT

An sh2 type corn which has a novel feature of having colored pericarp (pericarp layer) is provided. The corn is an sh2 type sweet corn, which is obtained by crossing Ruby Queen and an sh2 type sweet corn, and which has colored pericarp or pericarp containing antioxidant components.

8 Claims, 11 Drawing Sheets
(6 of 11 Drawing Sheet(s) Filed in Color)

(a) sweet corn (♀) x ENIW(♂)

(b) ENIW(♀) x sweet corn (♂)

(56) References Cited

OTHER PUBLICATIONS

All American Selections. Sweet Indian Summer F1. AAS Winners. 2000. Obtained Mar. 19, 2020 from https://all-americaselections.org/product/corn-sweet-indian-summer/. pp. 1.*

Hong et al. Anthocyanin composition and changes during kernel development in purple-pericarp supersweet sweetcorn. Food Chemistry. 2020. 315: pp. 1-8.*

Nielsen. Kernel Red Streak in Corn. Obtained from https://www.agry.purdue.edu/ext/corn/news/timeless/KernelRedStreak.html#:~:text=ernel%20red%20streak%2C%20or%20KRS,of%20an%20otherwise%20yellow%20kernel.&text=Researchers%20in%20South%20Dakota%20reported,during%20the%20grain%20filling%20period.Published 2017. pp. 1.*

Lee et al. Phenotypic and Genotypic Characterization of Purple Kernel Streak in White Food Corn. Crop Science. 2009. 49:1235-1241.*

John R. Laughnan, the Effect of the sh2 Factor on Carbohydrate Reserves in the Mature Endosperm of Maize, Genetics, Sep. 1953; 38(5): 485-499.

Janine R. Shaw et al., Genomic Nucleotide Sequence of a Wild type Shrunken-2 Allele of *Zea mays*, Plant Physiol. (1992) 98, 1214-1216.

Pericarp Studies in Maize. I. The Inheritance of Pericarp Colors. E. G. Anderson University of Michigan.

"Novel functionality of feed corn," the Japan Agri News, Jan. 7, 2016.

Burpee, "Corn, Ruby Queen Hybrid" https://www.burpee.com/vegetables/corn/corn-ruby-queen-hybrid-prod000673.html, Jan. 27, 2016.

English translation of "Novel functionality of feed corn," the Japan Agri News, Jan. 7, 2016 (2 pages).

Tracy, W.F., and Schmidt, D.H., Effect of Endosperm Type on Pericarp Thickness in Sweet Corn Inbreds, Crop Science, 1987, vol. 27, pp. 692-694.

Chopra, Surinder., et al., Alleles of the Maze P Gene with Distinct Tissue Specificities Encode Myb-Homologous Proteins with C-Terminal Replacements, The Plant Cell, 1996, vol. 8, pp. 1149-1158.

PCT International Search Report dated Dec. 19, 2017 issued in connection with corresponding PCT/JP2017/034823 (4 pages).

* cited by examiner

| | Name | Suger content (Brix) | |
|---|---|---|---|
| 1 | Gold Rush | 14.0 | |
| 2 | Gold Rush86 | 12.7 | |
| 3 | Gold Rush88 | 14.5 | |
| 4 | Yumeno corn | 14.3 | |
| 5 | Shiawase corn | 15.2 | |
| 6 | ENIW | 13.3 | |
| 7 | Ruby Queen | 21.8 | |

Fig. 5

| | Name | Starch (g/100g) | Fru (g/100g) | Glc (g/100g) | Suc (g/100g) |
|---|---|---|---|---|---|
| 1 | Gold Rush | 3.2 | 1.6 | 1.4 | 8.4 |
| 2 | Gold Rush86 | 4.4 | 1.6 | 1.5 | 7.3 |
| 3 | Gold Rush88 | 3.6 | 1.5 | 1.3 | 9.6 |
| 4 | Yumeno corn | 4.9 | 1.6 | 1.4 | 8.7 |
| 5 | Shiawase corn | 4.0 | 1.6 | 1.3 | 9.4 |
| 6 | ENIW | 7.3 | 2.0 | 1.7 | 7.5 |
| 7 | Ruby Queen | 2.7 | 1.1 | 1.1 | 2.9 |

Fig. 6

| | Name | Asp (mg/100g) | Glu (mg/100g) | Ala (mg/100g) | VC (mg/100g) | K (mg/100g) | Ca (mg/100g) | Fe (mg/100g) |
|---|---|---|---|---|---|---|---|---|
| 1 | Gold Rush | 63.3 | 153.4 | 171.5 | 10.8 | 279.0 | 9.2 | 0.5 |
| 2 | Gold Rush86 | 62.4 | 144.9 | 220.2 | 11.3 | 281.5 | 9.4 | 0.6 |
| 3 | Gold Rush88 | 65.7 | 126.1 | 186.2 | 10.0 | 272.8 | 10.3 | 1.0 |
| 4 | Yumeno corn | 63.7 | 149.7 | 166.2 | 10.5 | 257.9 | 10.3 | 0.8 |
| 5 | Shiawase corn | 59.6 | 104.0 | 109.5 | 9.5 | 262.9 | 9.6 | 0.8 |
| 6 | ENIW | 69.3 | 115.7 | 95.4 | 13.6 | 270.3 | 10.0 | 0.6 |
| 7 | Ruby Queen | 74.8 | 129.0 | 200.2 | 12.8 | 273.4 | 11.2 | 0.9 |

Fig. 7

| | Name | PP (mg/100g) | Anthocyanin (mg/100g) | DPPH(mg/100g): relative scale (Gold Rush=1.00) |
|---|---|---|---|---|
| 1 | Gold Rush | 85.5 | - | 1.00 |
| 2 | Gold Rush86 | 93.1 | - | 1.14 |
| 3 | Gold Rush88 | 95.4 | - | 1.10 |
| 4 | Yumeno corn | 105.5 | - | 1.35 |
| 5 | Shiawase corn | 109.8 | - | 1.45 |
| 6 | ENIW | 136.4 | 10.7 | 2.72 |
| 7 | Ruby Queen | 126.5 | 2.0 | 1.88 |

SWEET CORN AND METHOD FOR PRODUCING SAME

CROSS-REFERENCE TO RELATED APPLICATIONS

This application is a 371 of PCT/JP2017/034823, filed Sep. 21, 2017, which claims benefit of Japanese Patent Application No. 2016-186906 filed on Sep. 26, 2016.

TECHNICAL FIELD

The present invention relates to a corn which is classified as a sweet corn having novel traits (*Zea mays* var. *saccharata*) and a method for producing the same.

BACKGROUND ART

Corns are classified into, for example, the flint, flour, dent, pop, and sweet corns in accordance with types of endosperm in kernels. The sweet corn (*Zea mays* var. *saccharata*) is a mutant corn derived from the dent corn. Hereinafter, corns classified into the sweet type are sometimes simply referred to as "sweet corns." Sweet corns in the immature state are characterized by the highest sugar content in kernels and strong sweetness.

Conventionally, genetic mutations such as su1 (sugary-1), se (sugary enhancer), and sh2 (shrunken-2) have been employed for the improvement in sweetness of sweet corns. A sweet corn with sh2 among such genetic mutations, which is a so-called "super sweet corn," has a feature that it tends to leave sweetness in the mouth and has a long shelf-life as compared to sweet corns with other mutations such as su1 and se. Further, as another sh2 type genetic mutation, the sh2-i mutant gene has been known. There is a known sweet corn, which has been developed by a technique using this sh2-i mutant gene to improve germination under low temperatures, sugar content, and pericarp tenderness (Patent Literature 1).

For example, Non Patent Literature 1 discloses the influence of the sh2 mutant gene on the accumulation of carbohydrates in mature endosperm of corns and a mode of inheritance of the sh2 mutant gene. Further, Non Patent Literature 2 discloses the nucleotide sequence of the wild type sh2 allele and the amino acid sequence encoded by the nucleotide sequence.

Meanwhile, known color tones of kernels of the existing corns including sweet corns are yellow, white, orange, red, reddish brown, reddish purple, dark purple, and the like. For example, Non Patent Literature 3 discloses genetic analysis results of the color tone of the pericarp (pericarp layer) of corn kernels. According to Non Patent Literature 3, allelic traits of red, brown, white, cherry, and brownish cherry colors were verified. However, the corn disclosed in Non Patent Literature 3 is a dent corn, not a sweet corn. Further, a cultivar that has purple husk and stems as well as purple kernels has been developed for dent corns (Non Patent Literature 4).

Existing super sweet varieties have kernels with white, yellow, and purple color tones are known. These have the aleurone layer, i.e., the surface layer of endosperm, which is colored, meaning that the pericarp does not have a purple color. A variety having the se mutant gene, which is called "Ruby Queen," is known as a sweet corn having red kernels (Non Patent Literature 5).

CITATION LIST

Patent Literature

Patent Literature 1: JP Patent Publication (Kohyo) No. 2012-514471 A

Non Patent Literature

Non Patent Literature 1: John R. Laughnan, the Effect of the sh2 Factor on Carbohydrate Reserves in the Mature Endosperm of Maize, Genetics, 1953 September; 38(5): 485-499

Non Patent Literature 2: Janine R. Shaw et al., Genomic Nucleotide Sequence of a Wild type Shrunken-2 Allele of *Zea mays*, Plant Physiol. (1992) 98, 1214-1216

Non Patent Literature 3: PERICARP STUDIES IN MAIZE. I. THE INHERITANCE OF PERICARP COLORS. E. G. ANDERSON University of Michigan, Received Apr. 25, 1923

Non Patent Literature 4: "Novel functionality of feed corn," the Japan Agri News, Jan. 7, 2016

Non Patent Literature 5:
www dot burpee dot com/vegetables/corn/corn-ruby-queen-hybrid-prod000673 dot html.

SUMMARY OF INVENTION

Under the current circumstances, among sweet corns, most of sweet corns having the sh2 mutant gene (hereinafter referred to as a "super sweet corn" or "sh2 type" or "sh2 type sweet corn") are sweet corns having only yellow kernels (yellow corn), sweet corns having only white kernels (white corn), and sweet corns having white kernels and yellow kernels (bicolor variety). However, there have not been known sh2 type varieties having red or purple pericarp.

Therefore, the objective of the present invention is to provide an sh2 type corn, which has a novel feature of having colored pericarp (pericarp layer), and a method for producing such corn.

Solution to Problem

In view of the above circumstances, the present inventor made intensive studies and succeeded in fixing a trait of colored pericarp (pericarp layer) of kernels in sh2 type corns. This has led to the completion of the present invention. The present invention encompasses the following.

(1) A corn, which is an sh2 type sweet corn having colored pericarp.

(2) The corn according to (1), wherein the pericarp has a red color.

(3) The corn according to (1), wherein the red color of the pericarp is more purple than the color of Ruby Queen that is an se type sweet corn variety.

(4) The corn according to (1), wherein the pericarp is colored with flavonoids.

(5) The corn according to (4), wherein the flavonoids are anthocyanins.

(6) The corn according to (1), which is obtained by crossing a first breeding material and a second breeding material, wherein Ruby Queen that is an se type sweet corn variety is the first breeding material and a sh2 type sweet corn is the second breeding material.

(7) The corn according to (1), which is of Accession No. FERM BP-22309 or Accession No. FERM BP-22310 or is a progeny of Accession No. FERM BP-22309 or a progeny of Accession No. FERM BP-22310.

(8) A corn, which is an sh2 type sweet corn containing antioxidant components in its pericarp.

(9) The corn according to (8), wherein the antioxidant components are flavonoids.

(10) The corn according to (9), wherein the flavonoids are anthocyanins.

(11) The corn according to (8), wherein the contents of the antioxidant components are greater than those in pericarp of Ruby Queen that is an se type sweet corn variety.

(12) The corn according to (8), which is obtained by crossing a first breeding material and a second breeding material, wherein Ruby Queen that is an se type sweet corn variety is the first breeding material and an sh2 type sweet corn is the second breeding material.

(13) The corn according to (8), which is of Accession No. FERM BP-22309 or Accession No. FERM BP-22310 or is a progeny of Accession No. FERM BP-22309 or a progeny of Accession No. FERM BP-22310.

(14) A method for producing corn seeds, which comprises crossing the corn according to any one of (1) to (13) with an arbitrary corn.

(15) The method for producing corn seeds according to (14), which comprises designating the corn according to any one of (1) to (13) as a first breeding material and the corn according to any one of (1) to (13) as a second breeding material and breeding seeds obtained by crossing the first breeding material and the second breeding material, thereby producing an individual having colored pericarp or pericarp containing an antioxidant component.

(16) The method for producing corn seeds according to (14), wherein the corn according to any one of (1) to (13) is crossed with a corn having colorless pericarp, thereby producing seeds.

(17) The method for producing corn seeds according to (14), which comprises selecting an individual having colored pericarp or pericarp containing antioxidant components after the crossing.

(18) A corn or a progeny thereof, which has colored pericarp or pericarp containing antioxidant components obtained by the method for producing corn seeds according to any one of (14) to (17).

The present description includes part or all of the contents as disclosed in the description and/or drawings of Japanese Patent Application No. 2016-186906, which is a priority document of the present application.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Hereinafter, the corn and the method for producing the same according to the present invention will be described in detail with reference to the drawings.

The corn according to the present invention is an sh2 type sweet corn, has a feature that, of the tissues constituting a kernel, pericarp is colored. Further, the corn according to the present invention is an sh2 type sweet corn, has a feature that it has colored pericarp or pericarp containing antioxidant components.

Figure 1:
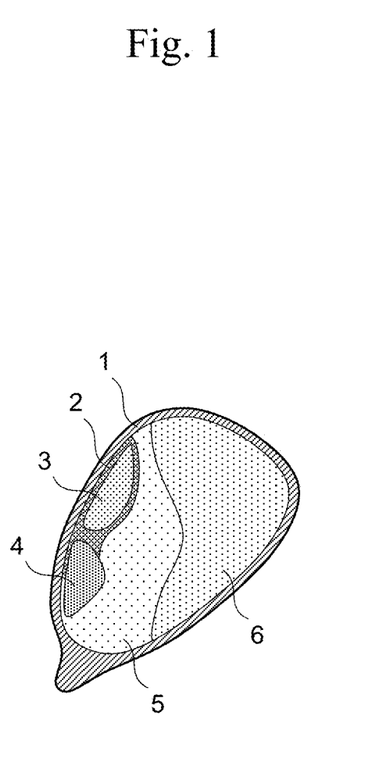
FIG. 1 is a schematic cross-sectional view of the inside of a corn kernel.

Here, each corn kernel has a structure illustrated in FIG. 1, in which a kernel is wrapped with pericarp 1. In a corn kernel, first leaf 3 protected by coleoptile 2, radicle 4, scutellum 5, and endosperm 6 are covered with pericarp 1 (FIG. 1). The term "pericarp" is also referred to as a "pericarp layer" and it means the outer layer of a kernel. The pericarp has a structure in which a plurality of layers are stacked.

The term "colored pericarp" used herein also means an embodiment in which one or two or more of the plurality of layers are colored and/or a portion between adjacent layers is colored. In addition, the expression "pericarp containing antioxidant components" used herein means an embodiment in which one or two or more of the plurality of layers each contain an antioxidant component and/or a portion between adjacent layers contains antioxidant components.

The term "colored pericarp" also means that the pericarp is chromatic. In particular, it means that the hue of the pericarp is within a yellow-red-purple range on a color wheel. The pericarp of the conventional sh2 type sweet corn is distinguished from the pericarp of the corn according to the present invention in that the color tone of the pericarp of the conventional sh2 type sweet corn is colorless to cloudy, which means that it is an achromatic color with translucency. In particular, the pericarp of the corn according to the present invention has a color tone which is preferably within a red-purple range and more preferably within a purplish red range. A high quality corn such as an sh2 type sweet corn with a beautiful color as well as an excellent taste can be obtained when the pericarp of the corn has a color within the above color range.

Note that Ruby Queen (se type sweet corn) which is an existing sweet corn variety has red pericarp. A comparison of the pericarp color tone between the corn according to the present invention and Ruby Queen suggests that the pericarp of the corn according to the present invention is characterized by a more purplish red color.

Furthermore, the antioxidant components contained in the pericarp are the above-mentioned components involved in coloring of pericarp, which mainly include flavonoids. However, the antioxidant components contained in the pericarp are not limited to flavonoids that cause coloring. Examples thereof may include ascorbic acid, tocopherol, carotene, and polyphenol compounds other than flavonoids.

In particular, as the antioxidant components, flavonoids that cause coloring are preferably contained. Among flavonoids, anthocyanins are more preferably contained. The term "flavonoid(s)" used herein collectively refers to compounds having a flavan skeleton, including a large number of compounds having a specific structure in which various functional groups bind to the skeleton. In addition, the term "anthocyanin(s)" used herein collectively refers to compounds having anthocyanidin as a basic skeleton, including a large number of compounds having a specific structure in which various functional groups and sugar chains bind to the anthocyanidin skeleton.

These antioxidant components are known to have the effect of improvement in the diseases related to aging, cancer, arteriosclerosis, and the like derived from the antioxidant activity. The corn according to the present invention contains these antioxidant components in the pericarp. Therefore, it can be used as a functional food or its ingredient with an expectation for such effect. Note that the antioxidant effects can be determined by a conventionally known method using corn kernels collected at a suitable harvest timing. As a method for measuring the antioxidant activity, there is a method for evaluating the antioxidant effect by determining the scavenging activity against DPPH (1,1-diphenyl-2-picrylhydrazyl). Alternatively, it is also possible to evaluate the antioxidant effect by quantifying the contents of polyphenol compounds and anthocyanin compounds in corn kernels collected at a suitable harvest timing.

Note that Ruby Queen that is an existing sweet corn variety (se type sweet corn) contains antioxidant components such as polyphenol compounds and anthocyanin compounds in its pericarp. When the corn according to the present invention is compared with Ruby Queen in terms of the amount of antioxidant components contained in pericarp and the antioxidant activity, the corn according to the present invention has a feature that its pericarp contains a larger amount of antioxidant components and it has excellent antioxidant activity. In particular, the corn according to the present invention has a feature that the anthocyanin content thereof is remarkably greater than that of Ruby Queen.

The sweet corn according to the present invention is an sh2 type sweet corn as described above, meaning that it has the sh2 gene (shrunken-2). sh2 type sweet corns are generally has a feature that the carbohydrate contents are higher than those of other types of sweet corns, and their shelf lives are relatively longer than those of conventional sweet corns. sh2 type sweet corns are also referred to as super sweet corns. JP Patent No. 5,727,384 discloses about sh2 type sweet corns in terms of comparison of characteristics with su type or se type sweet corns.

The sh2 gene is located on the long arm of chromosome 3 and encodes the large subunit of a class I enzyme ADP-glucose pyrophosphorylase (AGP). This enzyme is involved in the pathway of conversion from starch to sucrose. In addition, Janine R. Shaw et al., Genomic Nucleotide Sequence of a Wild type Shrunken-2 Allele Of *Zea mays*, Plant Physiol. (1992) 98, 1214-1216(Non Patent Literature 2) discloses the nucleotide sequence of the sh2 gene and the amino acid sequence of the protein encoded by the gene.

Dry seeds of sh2 type sweet corns exhibit a significantly shrunken appearance. This "shrunken" appearance of the dry seeds is different from the other types. In particular, the seed shape of sh2 type sweet corns has the following characteristics: 1: shrunken; 2: opaque or translucent; 3: relatively round shaped with a relatively deep recess. Regarding the seed shape of sh2 type sweet corns, "Boyer, C. D. and J. C. Shannon. 1983. The use of endosperm genes for sweet corn improvement. Plant Breeding Revs. 1: 139-161" can be referred to.

In addition, regarding the seed shape of se type sweet corns of Ruby Queen and the like described above, "Boyer, C. D. and J. C. Shannon. 1983. The use of endosperm genes for sweet corn improvement. Plant Breeding Revs. 1: 139-161" can also be referred to. In other words, se type sweet corns are described as follows: 1: the kernel color is pale (due to discoloration); 2: drying takes a longer time as compared with the su (sugary) variety. Further, se type sweet corns are characterized as follows as compared with sh2 type sweet corns: 1: the kernel color also tends to be pale; 2: the degree of transparency of kernels is greater (slightly translucent); 3: the upper part of each kernel has fine wrinkles which are prone to sharp wrinkles; 4: the kernels are less likely to shrink.

As described above, sh2 type sweet corns can be distinguished from other types of sweet corns by observing the kernel shape. It is also possible to distinguish sh2 type sweet corns from other types of sweet corns based on the nucleotide sequence of the sh2 gene disclosed in Janine R. Shaw et al., Genomic Nucleotide Sequence of a Wild type Shrunken-2 Allele Of *Zea mays*, Plant Physiol. (1992) 98, 1214-1216 (Non Patent Literature 2).

In addition, regarding the su gene and the sh2 gene, markers that are linked to the genes are known (Firoz Hossain et al., Mapping and validation of microsatellite markers linked to sugary 1 and shrunken2 genes in maize (*Zea mays* L.), J. Plant Biochem. Biotechnol. 2015, 24(2), 135-142). It is possible to distinguish sh2 type sweet corns from other types of sweet corns by utilizing these known microsatellite markers.

Further, it is known that when an sh2 type sweet corn is crossed with a non-sh2 type sweet corn, their progeny becomes the dent corn regardless whether the sh2 type sweet corn is a pollen parent or a seed parent. This phenomenon is not observed in sweet corns other than sh2 type sweet corns. Therefore, it is possible to determine whether or not a given sweet corn is of the sh2 type in a following way. When a progeny obtained by crossing the sweet corn with an existing sh2 type sweet corn and a progeny obtained by crossing the sweet corn with a sweet corn other than an existing non-sh2 type are produced, then if it is found that the former is a sh2 type sweet corn while the latter is a dent corn, the given sweet corn is regarded as the sh2 type.

As described above, the corn according to the present invention is an sh2 type sweet corn and has colored pericarp or pericarp containing an antioxidant component. Therefore, the corn according to the present invention has a feature that it exhibits very strong sweetness, has a vividly colored appearance, or has excellent antioxidant activities. In particular, in the case of the corn according to the present invention, since its pericarp is colored, the trait of coloring does not affect the other sh2 type sweet corns by so-called xenia. In other words, even when a different sh2 sweet corn is cultivated at a location close to that of the corn according to the present invention, the pericarp of the different sweet corn is not colored. Note that the term "xenia" refers to a phenomenon that double fertilization results in the influence of the paternal (pollen) gene on the traits of plant fruits or seeds. One example of xenia is the color of corn endosperm changes depending on the pollen line. This phenomenon can be induced not only in crossing between the dent corn and the sh2 type sweet corn but also in crossing between the se type sweet corn and the sh2 type sweet corn, which causes hardening of kernels and reduction of commercial values.

In addition, the corn according to the present invention has a feature that coloring of pericarp is darker than that in the se type Ruby Queen variety. Therefore, the corn according to the present invention has a feature that it has fewer variations in the color tone of each kernel and exhibits a uniform appearance as compared with Ruby Queen. As a result of measurement of the color of dry pericarp of Ruby Queen based on the R.H.S. Color Chart (The Royal Horticultural Society), the color was found to be closest to RED PURPLE GROUP 59 A. Meanwhile, the color of dry pericarp of the corn according to the present invention is closest to GREYED PURPLE GROUP N186 A.

Here, as the corn according to the present invention, it is possible to produce an sh2 type sweet corn with colored pericarp by growing a number of progenies, which can be obtained by crossing the se type Ruby Queen variety as a first breeding material and an existing sh2 type sweet corn as a second breeding material, and repeating self-crossing and backcrossing. As an example, seeds of the sh2 type sweet corn with colored pericarp created in the Examples below were internationally deposited on Jul. 20, 2016 under Accession Nos. FERM BP-22309 and FERM BP-22310 with NITE Patent Microorganisms Depositary, National Institute of Technology and Evaluation (#120, 2-5-8 Kazusakamatari, Kisarazu-shi, Chiba, Japan).

Further, it is possible to produce a novel corn by crossing the corn according to the present invention and an arbitrary corn. Here, the arbitrary corn is meant to include both a corn with non-colored pericarp (conventional corn) and the corn according to the present invention.

In other words, seeds obtained by crossing a corn according to the present invention (a first breeding material) and a corn according to the present invention (a second breeding material) are of an sh2 type sweet corn, which is a corn with an inherited trait of having colored pericarp or pericarp containing antioxidant components. This makes it possible to produce seeds of an sh2 type sweet corn with a feature of having colored pericarp or pericarp containing antioxidant components.

Note that the trait of having colored pericarp or pericarp containing antioxidant components is a trait derived from a seed parent. Thus, seeds obtained by crossing the corn according to the present invention serving as a seed parent with a different corn exhibit a trait of having colored pericarp or pericarp containing antioxidant components as a phenotype.

In general, when an sh2 type sweet corn is crossed with a non-sh2 type (su type or se type) corn, it results in production of a corn of the dent corn. Therefore, it is preferable to cross the corn according to the present invention with an sh2 type sweet corn. An sh2 type sweet corn belongs to, but is not particularly limited to, any of the yellow, bicolor, white, and tricolor varieties. Examples of such varieties that can be used include: yellow varieties such as Gold Rush, Miwakuno Corn (registered trademark), Mirai (registered trademark), Ohisama Corn (registered trademark), Picnic Corn (registered trademark), Mieru Corn, Kimihime (registered trademark), and Sunny Chocolat; bicolor varieties such as Kankanmusume (registered trademark), Honey Bantam (registered trademark), Cocktail (registered trademark), Peter Corn, Yumeno Corn (registered trademark), and Shiawase Corn (registered trademark); and tricolor varieties such as Woody Corn, which are varieties known in the art.

The present invention will be specifically described in the following examples. However, these examples are not intended to limit the scope of the present invention.

Example 1

In order to breed an sh2 type sweet corn with improved taste, detailed investigation of about 30 se type sweet corn varieties was conducted in 2006. At that time, it was found that coloring of pericarp results in red kernels for Ruby Queen with red kernels (hereinafter referred to as "RQ"). Since the pericarp of sh2 type sweet corns is transparent, when xenia occurs in terms of the endosperm color, it can be immediately distinguished by appearance. Meanwhile, since the pericarp of RQ is colored red, RQ has a feature that it does not cause xenia and the influence of xenia in RQ is not noticeable. Further, in a case in which an sh2 type sweet corn is fertilized with pollen of RQ or in a case in which RQ is fertilized with pollen of an sh2 type sweet corn, it is characteristic that xenia does not substantially influence the color of pericarp in either case.

In view of the above, breeding of a novel sh2 type sweet corn was started in 2006 and 2007. The breeding was conducted by crossing RQ line and 11 lines of sh2 type sweet corns as breeding materials. Between 2007 and 2014, self-crossing or backcrossing was repeatedly conducted with selection by seed forms characteristic to the sh2 type. As a result, it was observed that the degree of color development varies greatly depending on the sh2 type breeding material, and there are variations in the color development even in the same line depending on individuals. Therefore, procedures of selecting only 1 or 2 plants which were excellent in taste, color development, and cultivation characteristics from among 25 to 100 plants in each crossing were repeated over 7 years.

Eventually, two promising lines were selected among the obtained lines, which were SK-115R and SK-116R derived from crossing of SK-107P and Kimihime (registered trademark) included in the 11 sh2 breeding materials used herein with RQ. These two lines were obtained after repeating self-crossing or backcrossing about 10 times. The two lines were found to have a kernel form characteristic to the sh2 type while the characteristics of the se type were removed therefrom. In other words, the following characteristics of the se type were used as evaluation criteria: 1: the kernel color is pale (due to discoloration); 2: drying takes a longer time as compared with the su (sugary) variety (tendency not to shrink). In addition, the following characteristics of the se type were used as evaluation criteria for comparison with the sh2 type: 1: the kernel color also tends to be pale; 2: the degree of transparency of kernels is greater (slightly translucent); 3: the upper part of each kernel has fine wrinkles which are prone to sharp wrinkles; 4: the kernels are less likely to wilt.

Figure 2:
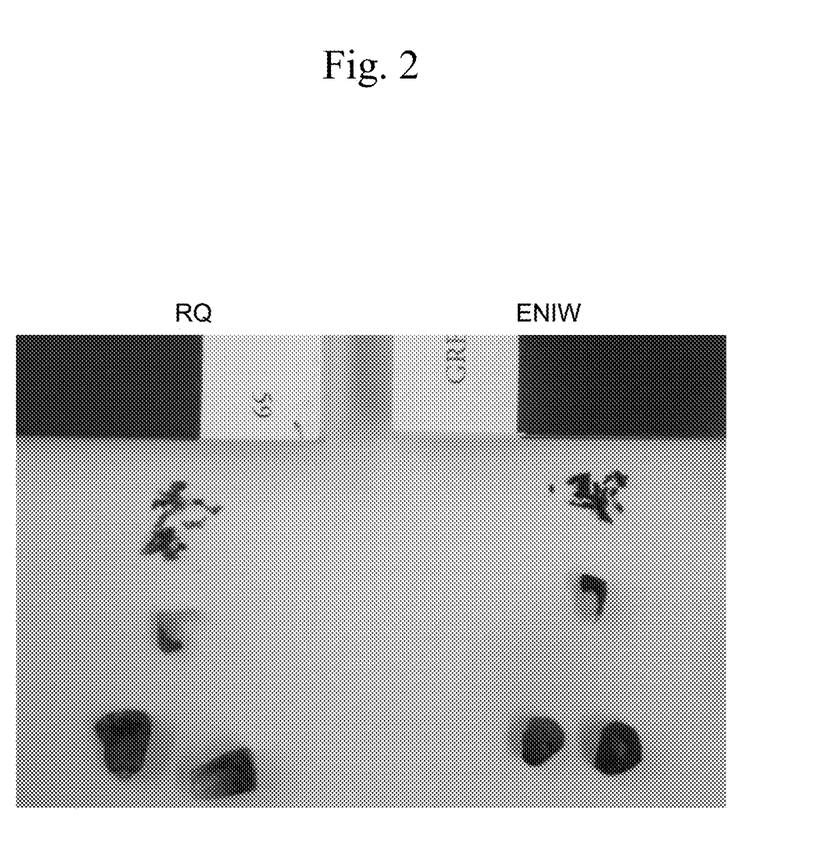
FIG. 2 is a photograph of dry kernels, removed pericarp portions, and partially peeled dry kernels of RQ and ENIW.

Through the steps described above, two breeding material with desirable traits, which were SK-115R and SK-116R could be developed. Surprisingly, the red color of the pericarp of F1 obtained by crossing SK-115R and SK-116R (hereinafter referred to as "ENIW") was significantly darker than that of RQ. FIG. 2 is a photograph of dry kernels, removed pericarp portions, and partially peeled dry kernels of RQ and ENIW. As shown in FIG. 2, as a result of color measurement based on the R.H.S. Color Chart (The Royal Horticultural Society), the color of the pericarp of dry kernels of RQ was closest to RED PURPLE GROUP 59 A. Meanwhile, the color of pericarp of dry kernels of ENIW was closest to GREYED PURPLE GROUP N186 A.

Figure 3:
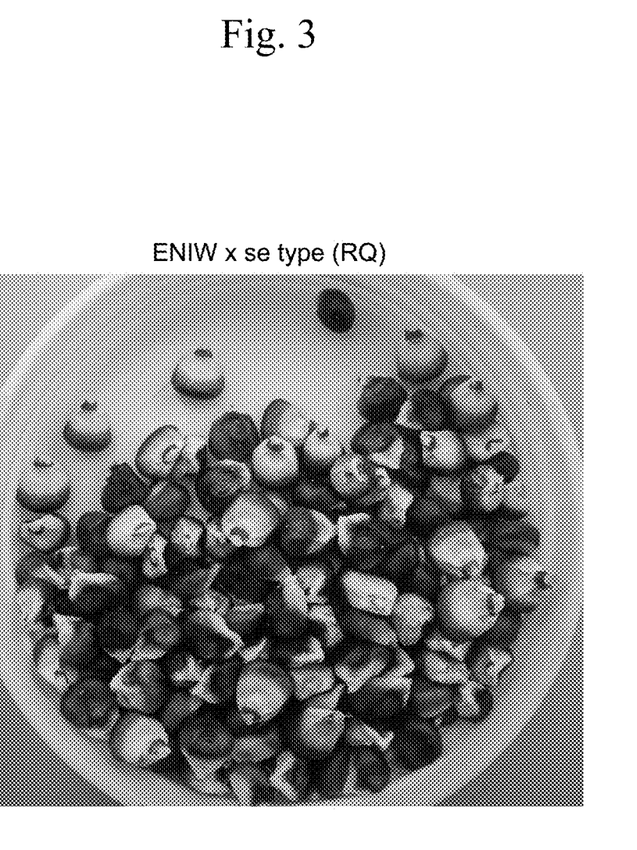
FIG. 3 is a photograph of a progeny obtained by crossing ENIW and the se type (RQ).

In addition, the progeny obtained by crossing ENIW and the se type (RQ) was confirmed to be of the dent corn (FIG. 3). Based on the above results, it was also confirmed that ENIW is an sh2 type sweet corn.

Seeds of SK-115R developed in this Example were internationally deposited on Jul. 20, 2016 under Accession No. FERM BP-22309 with NITE Patent Microorganisms Depositary, National Institute of Technology and Evaluation (#120, 2-5-8 Kazusakamatari, Kisarazu-shi, Chiba, Japan).

Seeds of SK-116R developed in this Example were internationally deposited on Jul. 20, 2016 under Accession No. FERM BP-22310 with NITE Patent Microorganisms Depositary, National Institute of Technology and Evaluation (#120, 2-5-8 Kazusakamatari, Kisarazu-shi, Chiba, Japan).

In the examination criteria for the current plant variety protection system of the Japanese Ministry of Agriculture, Forestry and Fisheries, for the tip portion of the corn kernel (Trait No. 44), there are 10 classes in a white to blue/purple/black range. However, white, yellow, and colors other than yellow are basically related to those other than the super sweet corn. Both SK-115R and SK-116R, which were grown in this Example, were found to correspond to class 8 (purple) according to the criteria.

Example 2

In this Example, component analysis of ENIW developed in Example 1, the existing sh2 type varieties, and RQ was conducted. The sh2 type varieties used in this Example were Gold Rush, Gold Rush 86, Gold Rush 88, Yumeno Corn (registered trademark), and Shiawase Corn (registered trademark).

First, these corn seeds were sown on Mar. 4, 2015 and grew by tunnel cultivation, and seeds were also sown on Apr. 9, 2015 and grew by mulching cultivation. In either cultivation method, harvesting was conducted when the accumulated temperature of average daily temperatures from the silking stage reached 500° C. (the optimum time point for normal sweet corn harvesting).

Thereafter, some of kernels were collected, and sugar content analysis, component analysis, and radical scavenging activity analysis per fresh weight of 100 g were performed. In component analysis, HPLC was performed for the following: Fru: fructose, Glc: glucose, Suc: sucrose, Asp: aspartic acid, Glu: glutamic acid, and Ala: alanine. The colorimetric method was performed for the following: VC: vitamin C, K: potassium, Ca: calcium, Fe: iron, and PP: polyphenols and anthocyanins. The weight method was performed for starch. Further, the scavenging activity against 1,1-diphenyl-2-picrylhydrazyl (DPPH) was determined by radical scavenging activity analysis.

Figure 4:
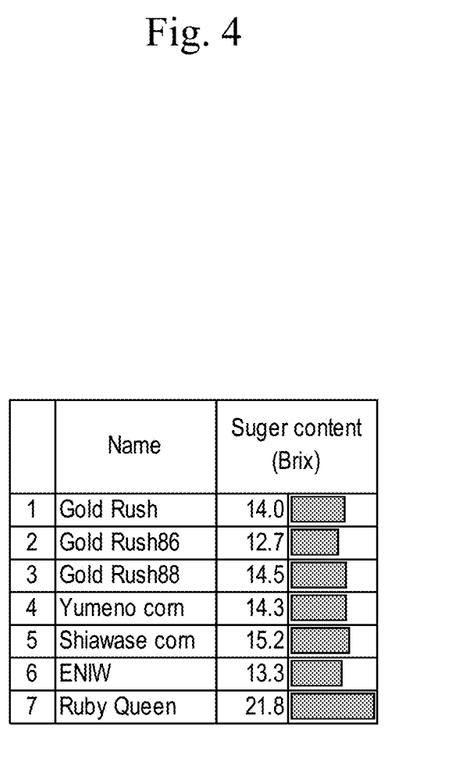
FIG. 4 is a characteristic diagram indicating the analysis results of sugar contents in ENIW, the existing sh2 type, and RQ.
Figure 5:
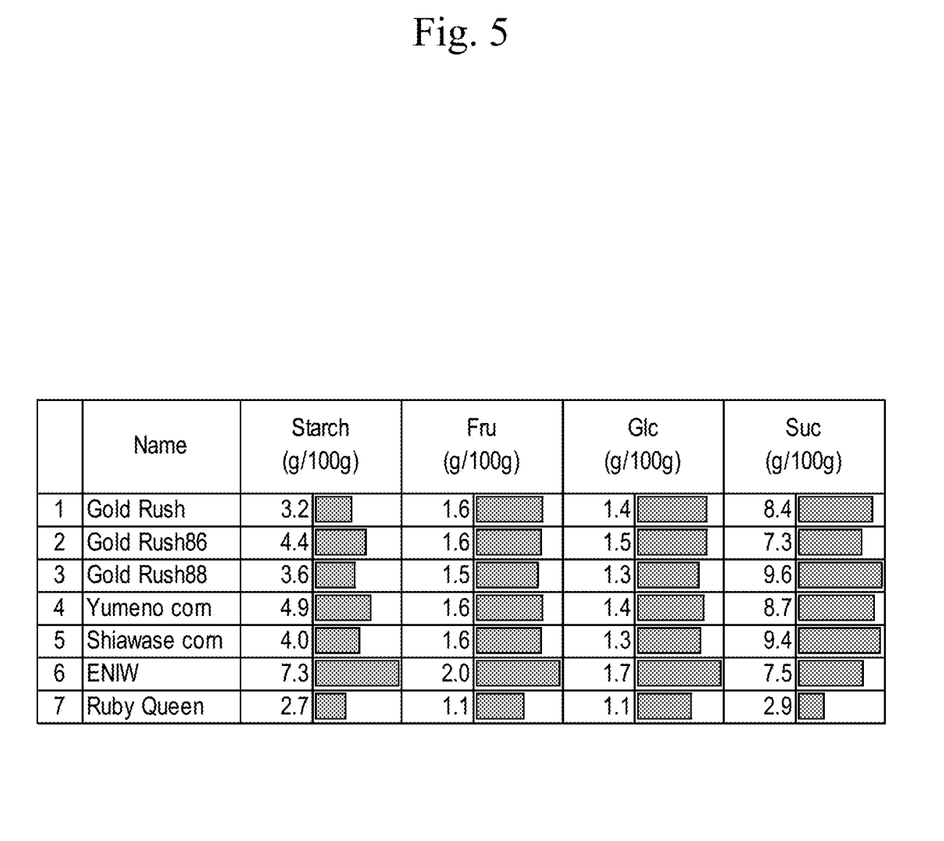
FIG. 5 is a characteristic diagram indicating the analysis results of components in ENIW, the existing sh2 type, and RQ.
Figure 6:
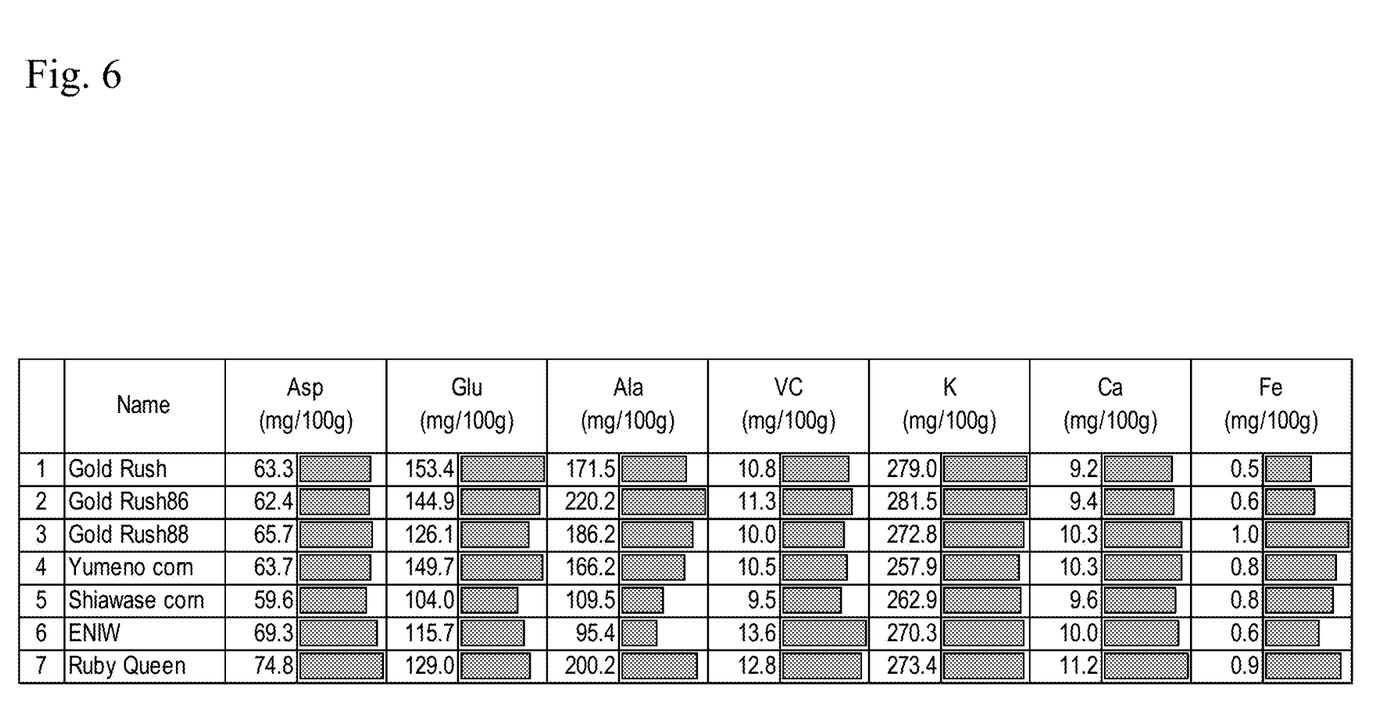
FIG. 6 is a characteristic diagram indicating the analysis results of components in ENIW, the existing sh2 type, and RQ.
Figure 7:
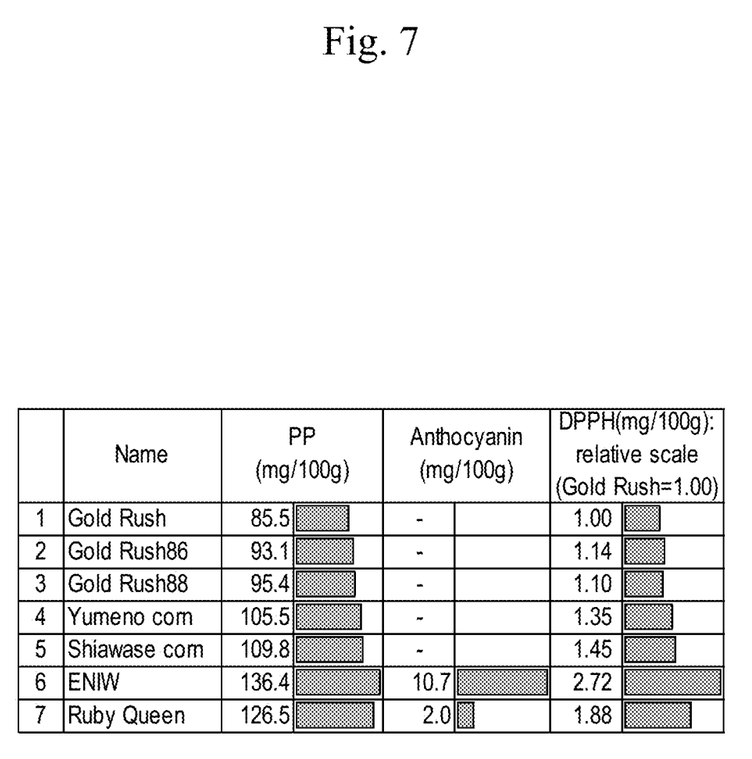
FIG. 7 is a characteristic diagram indicating the analysis results of components and radical scavenging activity in ENIW, the existing sh2 type, and RQ.

FIG. 4 indicates the results of sugar content analysis. FIGS. 5 to 7 indicate the results of component analysis. FIG. 7 indicates the results of radical scavenging activity analysis. The results of FIGS. 4 to 7 indicate the average values of analysis values of the harvest of tunnel cultivation and analysis values of the harvest of mulching cultivation. In addition, for Nos. 1 to 5, anthocyanin component analysis was omitted because the red color could not be visually observed.

As shown in FIGS. 5 to 7, ENIW was revealed to contain components equivalent to or greater than those in the other sh2 type varieties. Further, as indicated in FIGS. 5 to 7, it was revealed that the contents of major sugar components and especially polyphenols in ENIW were significantly higher than those in RQ, and the anthocyanins in ENIW were significantly higher by approximately 5 times than that in RQ. Note that although the sugar content in Ruby Queen is higher than that in ENIW, this is probably because Ruby Queen contains a lot of glycogen. Furthermore, as indicated in FIG. 7, it was found that ENIW has radical scavenging activity at a level significantly higher than that in other sh2 type varieties and RQ.

The above results revealed that ENIW not only has the taste comparable to that of the usual sh2 type but also contains the characteristic components described above. As stated above, since the anthocyanins in ENIW are remarkably greater than that in RQ, for example, ENIW is considered to be useful for preventing aging, cancer, and lifestyle diseases such as arteriosclerosis and thus used for various applications such as colors for cuisine, dyes, functional components, and the like because of its appearance. In addition, as stated above, since ENIW has a feature that it does not affect the kernel colors of usual super sweet varieties, for example, it is easy for producers to cultivate ENIW, and they may be able to sell a combination of ENIW and a usual sh2 variety with a beautiful contrast of kernel colors, thereby improving the consumer appetite.

Example 3

Figure 8:
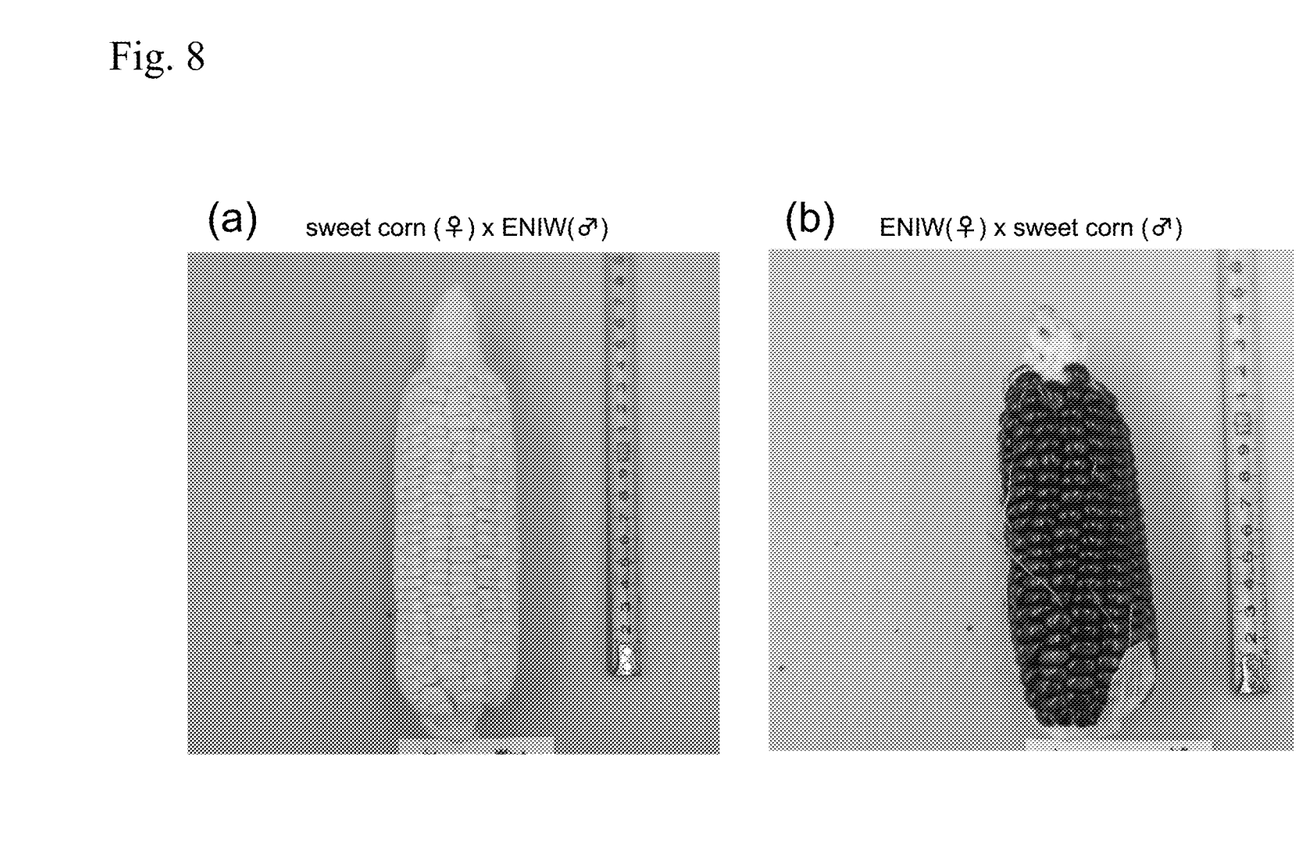
FIG. 8 shows photographs of progenies produced by crossing with the use of ENIW as a seed parent or pollen parent.

In this Example, the occurrence of xenia was verified using ENIW developed in Example 1. First, seeds were sown to start tunnel cultivation on Mar. 4, 2015. Ears of a usual sh2 type sweet corn (variety name: Gold Rush) were pollinated using ENIW as a pollen parent between May 19 and May 21. In addition, ENIW as a seed parent and an sh2 type (variety name: Gold Rush) as a pollen parent were crossed. Photographs of the hybrid progeny obtained using ENIW as a pollen parent and the hybrid progeny obtained using ENIW as a seed parent are shown in FIGS. 8(a) and 8(b), respectively. As shown in FIG. 8(a), in the case of ENIW used as a pollen parent, no xenia occurred in the resulting hybrid progeny. On the other hand, as shown in FIG. 8(b), in the case of the hybrid progeny obtained using ENIW as a seed parent, although yellow endosperm was supposed to be partially formed theoretically due to xenia, the colored pericarp thereof did not actually affect the appearance of the progeny, and therefore, xenia did not substantially influence the appearance.

Example 4

Figure 9:
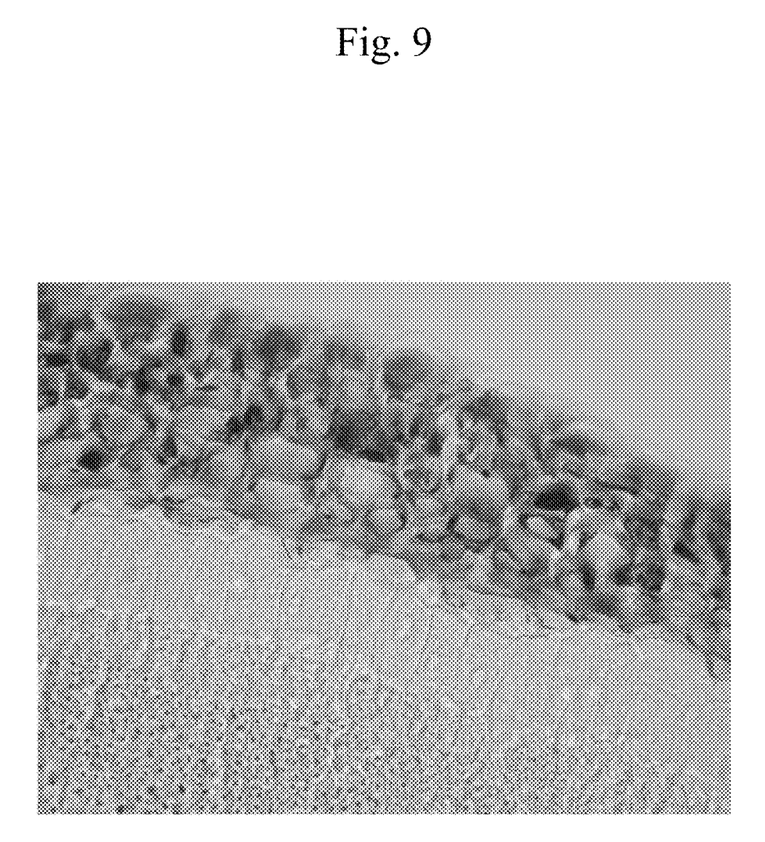
FIG. 9 is a photograph of an unstained sectioned kernel of ENIW.

In this Example, detailed observation of ENIW developed in Example 1 was conducted. First, a kernel of ENIW developed in Example 1 was sectioned in the following manner. A collected kernel was immersed in FAA fixative solution for fixation. Thereafter, the kernel was dehydrated and embedded in Paraplast® (a mixture of an embedding agent, paraffin, and a resin). Sections thereof were prepared using a microtome. At such time, the thickness was set to 10 to 25 μm using a rotary microtome. The resulting sections were left unstained or stained by the Stoughton method and photographed. In photography, a microscope (Olympus BX-50) was used, and shooting was conducted with an Olympus FX-38 digital photography apparatus. FIG. 9 is a photograph of the resulting section.

As shown in FIG. 9, coloring of kernel pericarp (pericarp layer) was observed while coloring of layers inside of the pericarp was not observed. Thus, it was revealed that the pericarp, which is transparent in the existing sh2 type sweet corn, that is to say, a portion that is not influenced by xenia, was exclusively colored in ENIW developed in Example 1.

Figure 10:
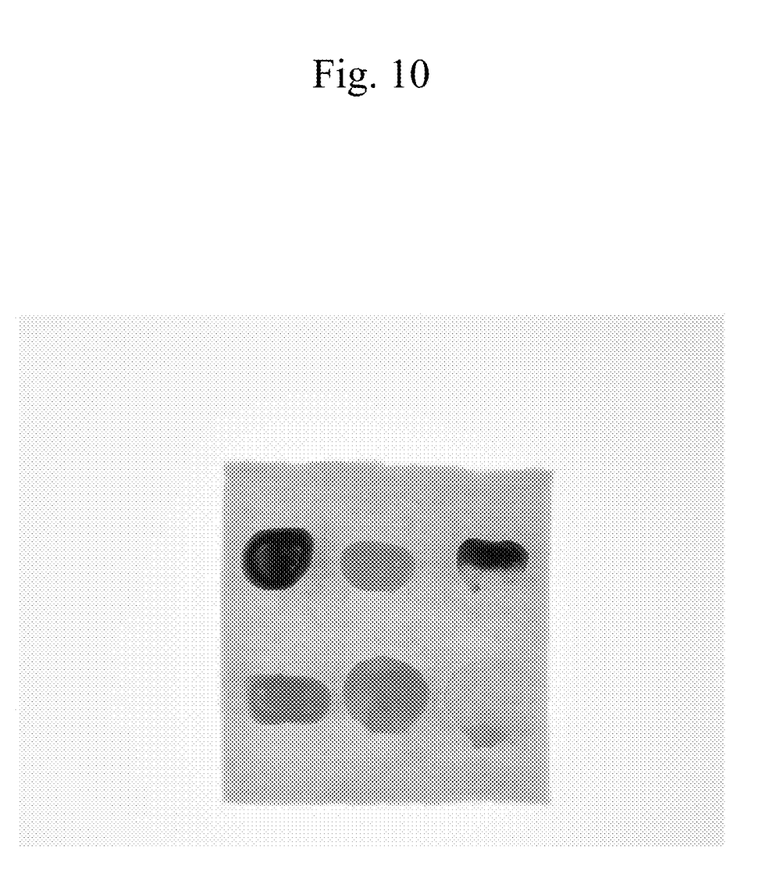
FIG. 10 is a photograph of kernels, peeled kernels, and removed pericarps of ENIW and Gold Rush.

Further, in this Example, kernels, peeled kernels, and removed pericarp of ENIW developed in Example 1 and Gold Rush as an existing sh2 type sweet corn were photographed. FIG. 10 indicates the results. In the photograph shown in FIG. 10, the upper part corresponds to ENIW and the lower part corresponds to Gold Rush. Further, in the photograph shown in FIG. 10, the left column corresponds to harvested kernels, the middle column corresponds to peeled kernels, and the right column corresponds to removed pericarp.

As shown in FIG. 10, it was revealed that the pericarp of the existing sh2 type sweet corn is transparent while the interior covered by the pericarp has a yellow color. Meanwhile, the pericarp of ENIW is red and the interior covered by the pericarp is white (sometimes yellow due to xenia).

Figure 11:
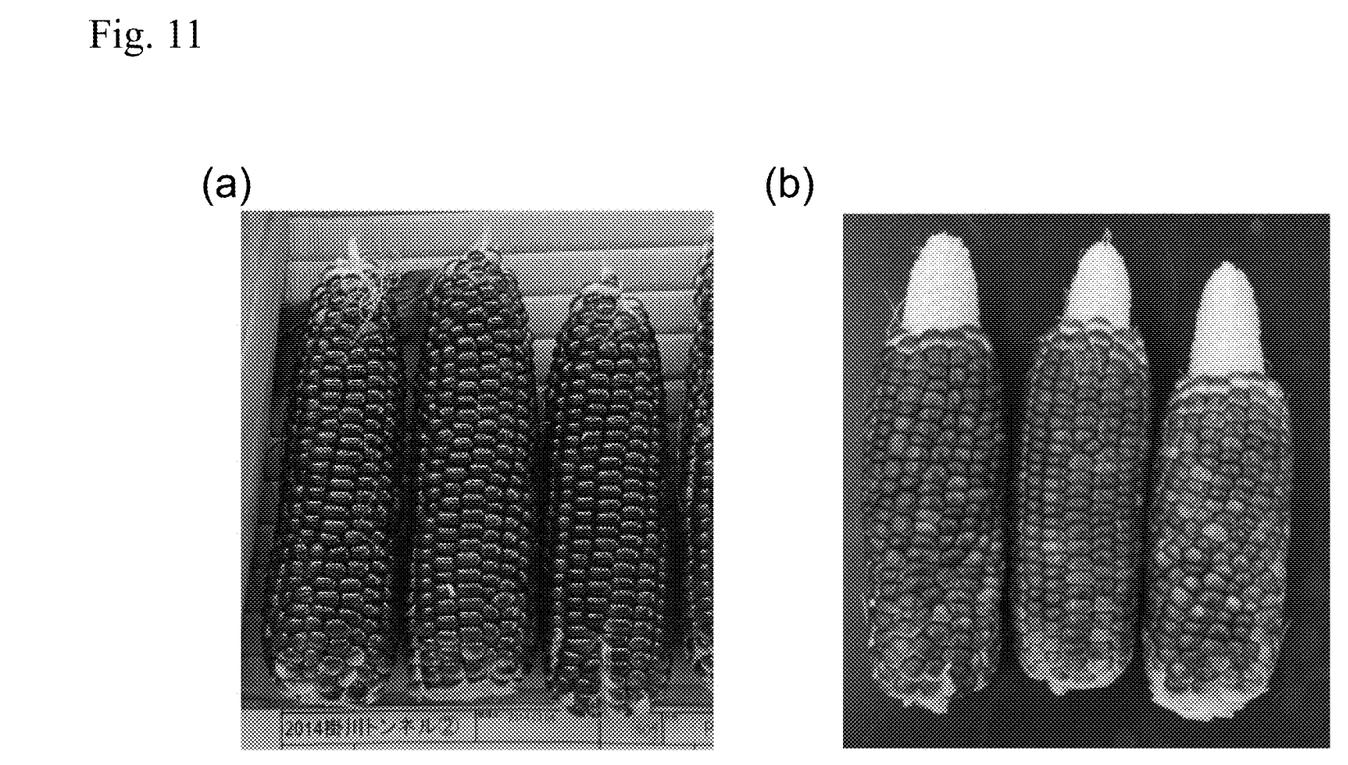
FIG. 11 shows photographs of ears of ENIW and Ruby Queen.

Further, in this Example, the full-length ears were photographed for ENIW grown in Example 1 and the existing RQ. FIG. 11 indicates the results. In FIG. 11(a) shows the ears of ENIW and FIG. 11(b) shows the ears of RQ. As a result of comparison of FIGS. 11(a) and 11(b), it is understood that the ears of ENIW exhibit a uniform red color as compared to the ears of RQ. In other words, ENIW developed in Example 1 has a uniform red color in comparison of individual kernels. Thus, it can be said that ENIW has excellent commercial values over RQ.

Based on the above results, it was confirmed that ENIW developed in Example 1 is an sh2 type sweet corn, which is a novel corn having red pericarp and containing antioxidant components in the pericarp.

INDUSTRIAL APPLICABILITY

The corn according to the present invention has a novel feature that it has colored pericarp among tissues constituting a kernel, which is not imparted to conventional sh2 type sweet corns. Therefore, the corn according to the present invention, which is a high sugar content variety, has an excellent taste as in the case of the conventional sh2 type sweet corns, and it exhibits a characteristic appearance due to coloring of the pericarp.

In addition, the corn according to the present invention has a novel feature that it contains antioxidant components in the pericarp, which is not imparted to conventional sh2 type sweet corns. Therefore, the corn of the present invention, which is a high sugar content variety, has an excellent taste as in the case of the conventional sh2 type sweet corns, and it can maintain functionality of the antioxidant components.

Further, according to the method for producing a corn according to the present invention, it is possible to produce a corn with a feature of having colored pericarp among tissues constituting a kernel or a feature of containing antioxidant components in the kernel.

All publications, patents and patent applications cited in the present description are incorporated herein by reference in their entirety.

The invention claimed is:

1. A seed of sh2-type sweet corn variety SK-115R, wherein representative seed of said variety has been deposited under Accession No. FERM BP-22309.

2. A plant grown from the seed of claim 1.

3. A seed of sh2-type sweet corn variety SK-116R, wherein representative seed of said variety has been deposited under Accession No. FERM BP-22310.

4. A plant grown from the seed of claim 3.

5. A seed of hybrid sh2-type sweet corn variety ENIW, that is produced by crossing a first plant of variety SK-115R with a second plant of variety SK-116R, wherein representative seed of said varieties SK-115R and SK-116R have been deposited under Accession Nos. FERM BP-22309 and FERM BP-22310, respectively.

6. A plant grown from the seed of claim 5.

7. A method of producing hybrid sh2-type sweet corn variety EINW comprising crossing a first plant of variety SK-115R with a second plant of variety SK-116R, wherein representative seed of said varieties SK-115R and SK-116R have been deposited under Accession Nos. FERM BP-22309 and FERM BP-22310, respectively.

8. A hybrid sh2-type sweet corn plant of variety ENIW produced by the method of claim 7, wherein the pericarp of the hybrid sh2-type sweet corn of variety ENIW exhibits a red color that is darker than the se type se sweet corn variety Ruby Queen pericarp.

* * * * *